(12) United States Patent
Cabiri et al.

(10) Patent No.: US 10,898,642 B2
(45) Date of Patent: Jan. 26, 2021

(54) PATCH INJECTOR

(71) Applicant: West Pharma. Services IL, Ltd., Ra'anana (IL)

(72) Inventors: Oz Cabiri, Hod Hasharon (IL); Ran Hezkiahu, Herzliya (IL); Tal Hammer, Ramat-Gan (IL)

(73) Assignee: WEST PHARMA. SERVICES IL, LTD., Ra'anana (IL)

( * ) Notice: Subject to any disclaimer, the term of this patent is extended or adjusted under 35 U.S.C. 154(b) by 0 days.

(21) Appl. No.: 16/645,910

(22) PCT Filed: Sep. 17, 2018

(86) PCT No.: PCT/US2018/051337
§ 371 (c)(1),
(2) Date: Mar. 10, 2020

(87) PCT Pub. No.: WO2019/055916
PCT Pub. Date: Mar. 21, 2019

(65) Prior Publication Data
US 2020/0276384 A1    Sep. 3, 2020

Related U.S. Application Data

(60) Provisional application No. 62/559,107, filed on Sep. 15, 2017.

(51) Int. Cl.
*A61M 5/142* (2006.01)
*A61M 5/145* (2006.01)
*A61M 5/158* (2006.01)

(52) U.S. Cl.
CPC ...... *A61M 5/14248* (2013.01); *A61M 5/1452* (2013.01); *A61M 5/158* (2013.01);
(Continued)

(58) Field of Classification Search
CPC .... A61M 2005/206; A61M 2005/3289; A61M 5/1454; A61M 5/14244; A61M 5/14248;
(Continued)

(56) References Cited

U.S. PATENT DOCUMENTS 5,858,001 A * 1/1999 Tsals ................. A61M 5/14248
604/135
2013/0296824 A1   11/2013 Mo et al.

FOREIGN PATENT DOCUMENTS

WO    9721457 A1    6/1997
WO    9857683 A1    12/1998
(Continued)

OTHER PUBLICATIONS

Int'l Preliminary Report on Patentability dated Oct. 24, 2019 in Int'l Application No. PCT/US2018/051337.
(Continued)

*Primary Examiner* — Bhisma Mehta
*Assistant Examiner* — Hong-Van N Trinh
(74) *Attorney, Agent, or Firm* — Panitch Schwarze Belisario & Nadel LLP

(57) ABSTRACT

A patch injector (10) for parenteral administration of a drug to a drug recipient has a drug-cartridge module (14) attached to a power-pack module (12) and to a drug-recipient interface module (16). A compressed, elastic power element (18) disposed in the power-pack module (12) is coupled to a plunger (30) movably disposed in a drug reservoir (22) in the drug-cartridge module (14). An injection needle (24) at the distal end of the drug reservoir (22) is oriented orthogonal to the drug reservoir (22) and generally toward a skin-contact surface (28) extending parallel to the longitudinal drug-reservoir axis (22A). The power element (18) is configured to displace the plunger (20) distally into the drug reservoir (22) and to move the injection needle (24) toward the
(Continued)

skin-contact surface (28) when the power element (18) expands distally along the drug-reservoir axis (22A).

5 Claims, 8 Drawing Sheets

(52) U.S. Cl.
CPC ............. *A61M 2005/14506* (2013.01); *A61M 2005/1585* (2013.01)

(58) Field of Classification Search
CPC ......... A61M 2005/14252; A61M 2005/14256; A61M 2005/1426; A61M 2005/1581; A61M 5/158; A61M 2005/1585; A61M 5/1452; A61M 5/145; A61M 2005/14506; A61M 5/142
See application file for complete search history.

(56) References Cited

FOREIGN PATENT DOCUMENTS

| | | |
|---|---|---|
| WO | 2013032841 A1 | 3/2013 |
| WO | 2015118358 A1 | 8/2015 |
| WO | 2017127215 A1 | 7/2017 |
| WO | 2017127216 A1 | 7/2017 |

OTHER PUBLICATIONS

Int'l Search Report and Written Opinion dated Dec. 10, 2018 issued Int'l Application No. PCT/US2018/051337.

\* cited by examiner

PATCH INJECTOR

CROSS-REFERENCE TO RELATED APPLICATIONS

This application is a section 371 of International Application No. PCT/US2018/051337, filed Sep. 17, 2018, which was published on Mar. 21, 2019 under International Publication No. WO 2019/055916 A1, and which claims priority from U.S. Provisional Patent Application No. 62/559,107 filed on Sep. 15, 2017, the contents of each of which are incorporated herein by reference.

BACKGROUND OF THE INVENTION

The present invention relates to a patch injector for parenteral administration of a drug to a drug recipient. More particularly, the present invention is directed to a modular injection device that is completely mechanically powered and driven by a single stored power source to facilitate filling, assembly, and parenteral administration of a drug to the drug recipient.

The conventional method of parenteral administration of a drug to a drug recipient is by injection using a hypodermic syringe. A number of difficulties associated with these syringes have led to attempts to derive more advantageous drug delivery devices. Syringes are not generally advocated for use in self administration by patients because of the dangers of embolisms arising from the introduction of air bubbles into the bloodstream, incorrect dosing, and the accidental infection of third parties after use of the syringe.

Pen injectors have a coaxial relationship between the syringe and the injection needle. Such injectors may include a high profile (with a long axis perpendicular to the skin during injection). Many applications, (for example large and/or high viscosity payloads) are better suited to low profile and or wearable patch injectors.

U. S. Patent Application Publication No. 2013/0296824 A1 (Mo et al.) discloses a microneedle based transdermal drug delivery device including a bottom portion hingeably connected to a top portion. The top portion includes at least one needle connected to at least one corresponding hollow chamber in which a medicament or medicament cartridge is stored. When activated by a drug recipient, the top portion is pivoted by the drug recipient's hand towards the bottom portion until the needle pierces the drug recipient's skin. Springs then drive a plunger through the hollow chambers to dispense the medicament to the drug recipient.

Accordingly, there is a need in the art for a small, inexpensive, prefillable and wearable injector that delivers a drug from a cartridge with minimal operator intervention and is entirely mechanically powered.

BRIEF SUMMARY OF THE INVENTION

Briefly stated, one embodiment of the present invention is directed to a patch injector (10) for parenteral administration of a drug to a drug recipient having a skin surface. The patch injector (10) comprises a drug-cartridge module (14) having a drug reservoir (22) with a longitudinal drug-reservoir axis (22A). A plunger (30) is movably disposed in the drug reservoir (22). A power-pack module (12) is attached to the proximal end of the drug-cartridge module (14). A compressed, elastic power element (18) is disposed in the power-pack module (12) and coupled to the plunger (30). The compressed, elastic power element (18) is expandable along the drug-reservoir axis (22A). A drug-recipient interface module (16) is connected to the power-pack module (12). The drug-recipient interface module (16) comprises a skin-contact surface (28) extending parallel to the drug-reservoir axis (22). An injection needle (24) is disposed at the distal end of the drug reservoir (22), is in fluid communication with the drug reservoir (22) and is oriented orthogonal to the drug reservoir (22) and generally toward the skin-contact surface (28). An injection-needle insertion mechanism (58) is driven by the compressed, elastic power element (18). The compressed, elastic power element (18) is configured to displace the plunger (20) distally into the drug reservoir (22) and to move the injection needle (24) toward the skin-contact surface (28) when the compressed, elastic power element (18) expands distally along the drug-reservoir axis (22A).

Another embodiment of the present invention is directed to a method for parenteral administration of a drug to a drug recipient having a skin surface comprising the steps of: attaching a skin-contact surface of a patch injector to the skin surface of a drug recipient; releasing a portion of a compressed, elastic power element disposed in a power-pack module of the patch injector to exit the power-pack module; expanding the compressed, elastic power element outwardly from the power-pack module substantially parallel to the skin-contact surface; driving a needle insertion mechanism of the patch injector with the expanding compressed, elastic power element to extend an injection needle tip outwardly from said skin contact surface to penetrate the skin surface of the drug recipient; displacing a plunger disposed in a drug reservoir of the patch injector having the drug therein with the expanding compressed, elastic power element to discharge the drug through the injection needle tip; and driving a needle protection mechanism of the patch injector with the expanding compressed, elastic power element to protect the injection needle tip with a needle shield upon withdrawal of the injection needle tip from the skin surface of the drug recipient.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, the drawings show embodiments which are presently preferred. It should be understood, however, that the invention is not limited to the precise arrangements and instrumentalities shown.

In the drawings.

DETAILED DESCRIPTION OF THE INVENTION

Figure 1:
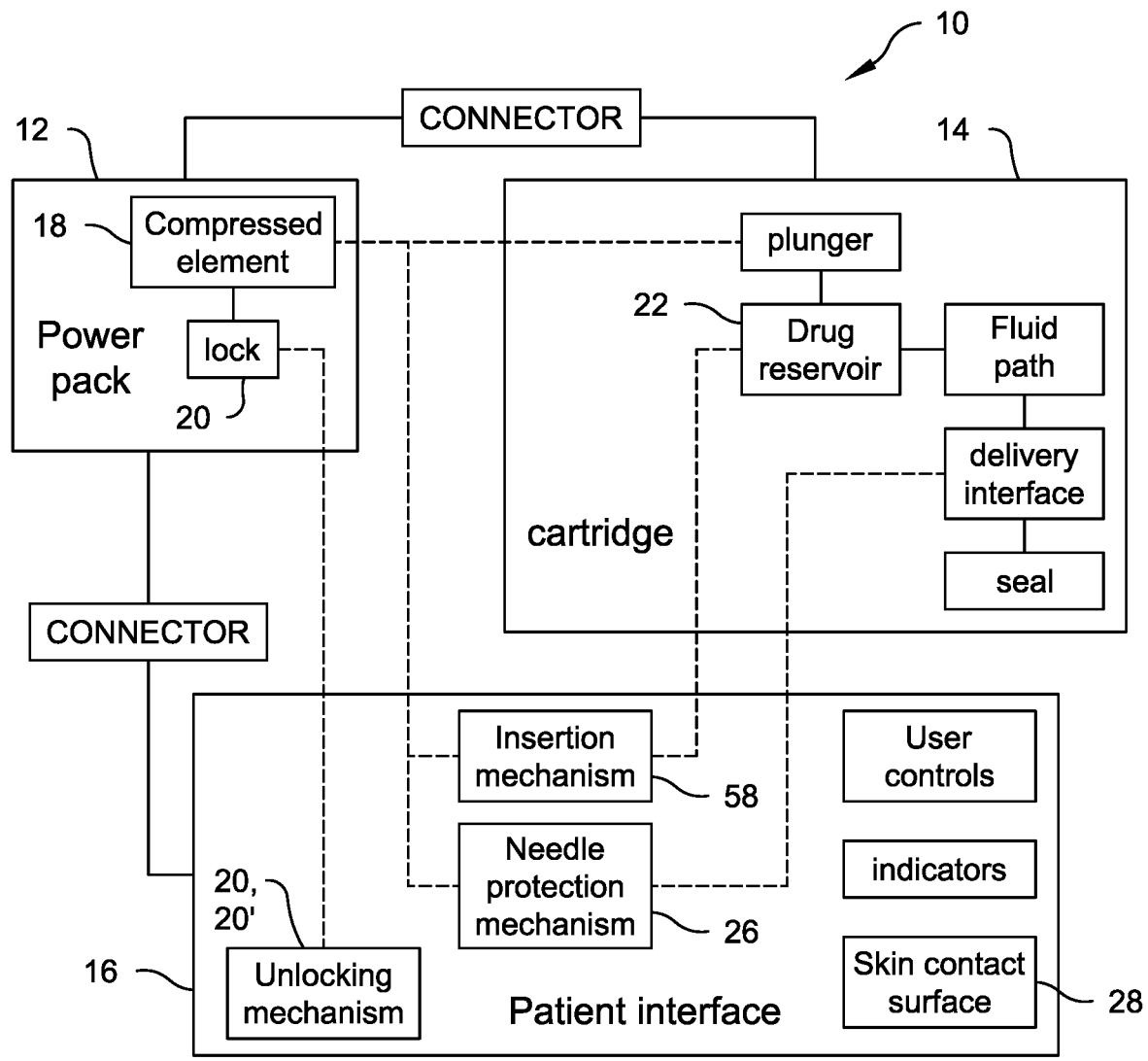
FIG. 1 is a schematic diagram of a first preferred embodiment of a patch injector in accordance with the present invention.
Figure 2:
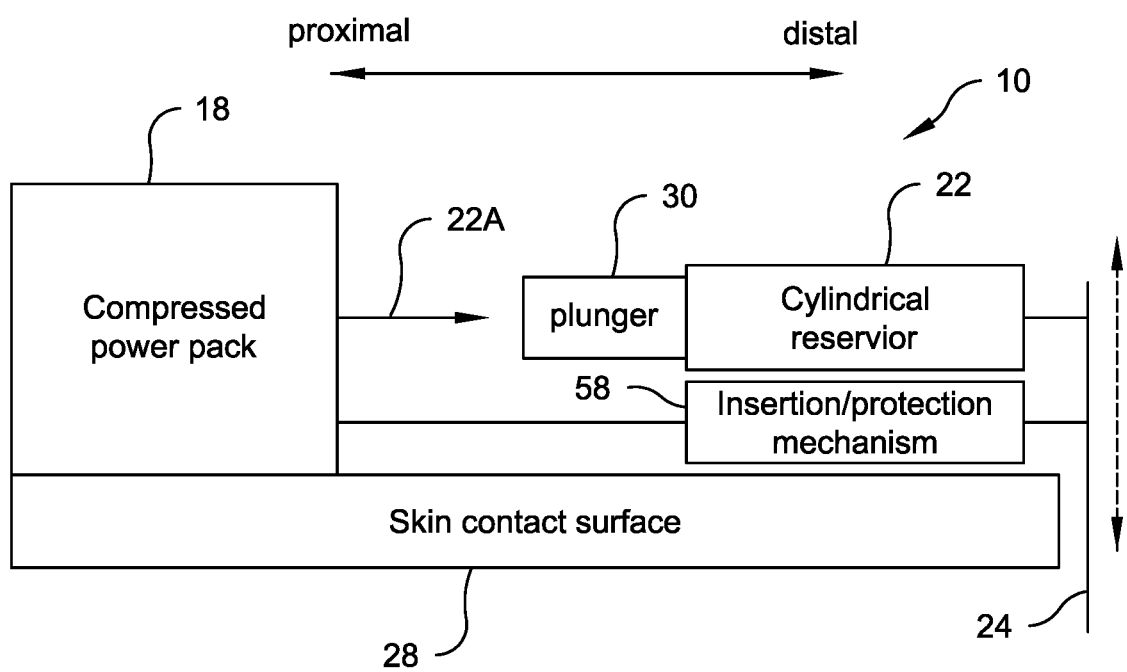
FIG. 2 is a block diagram of the patch injector of FIG. 1.

Reference will now be made in detail to embodiments of the invention, examples of which are illustrated in the accompanying drawings. The terminology used in the description of the invention herein is for the purpose of describing particular embodiments only and is not intended to be limiting of the invention.

As used in the description of the invention and the appended claims, the singular forms "a", "an" and "the" are intended to include the plural forms as well, unless the context clearly indicates otherwise. The words "and/or" as used herein refers to and encompasses any and all possible combinations of one or more of the associated listed items. The words "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The words "right," "left," "lower" and "upper" designate directions in the drawings to which reference is made. The words "inwardly" and "outwardly" refer to directions toward and away from, respectively, the geometric center of the patch injector, and designated parts thereof. The terminology includes the words noted above, derivatives thereof and words of similar import.

As used herein, the words "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

The following description is directed towards various embodiments of a patch injector in accordance with the present invention.

Referring to the drawings in detail, where like numerals indicate like elements throughout, there is shown in FIGS. 1-5 a first preferred embodiment of the patch injector, generally designated 10, and hereinafter referred to as the "patch injector" 10 in accordance with the present invention. The patch injector 10 is directed to a modular injection device that is completely mechanically powered and driven by a single compressed, elastic power source to facilitate filling, assembly, and distribution of the injector.

The patch injector 10 comprises a power-pack module 12 connected to a drug-cartridge module 14 and to a drug-recipient (or patient) interface module 16. The power-pack module 12 includes a compressed, elastic power element 18, such as a linear or bent spring (see, e.g., International Application Publication Number WO 2018/136194, incorporated herein by reference), and a locking element 20 which prevents unintentional activation of the power element 18. The drug-cartridge module 14 includes a drug reservoir 22, with a drug-reservoir axis 22A (see FIG. 2) parallel to the skin surface of the drug recipient to minimize the profile of the patch injector 10. The drug-recipient interface module 16 includes an injection needle 24, a needle shield 26, and a skin-contact surface 28 running parallel to the drug-reservoir axis 22A, an injection-needle insertion mechanism 58, and a needle protection mechanism 60. The interface module 16 may include indicators which may be mechanical indicators or electronic status indicators. The indicators may indicate a delivery status such as delivery of the drug, non-delivery of the drug, a completed delivery or a failed delivery. Also, the interface module 16 may include user controls which may include an activation switch 44 discussed in more detail below.

The power-pack module 12 is located at and attached to the proximal end of the drug-cartridge module 14. The compressed, elastic power element 18 is coupled to a plunger 30 disposed in the drug reservoir 22 and is selectively prevented from activation by the locking element 20. When the patch injector 10 is activated, the compressed, elastic power element 18 expands along the drug-reservoir axis 22A to displace the plunger 30 distally into the drug reservoir 22. At the distal end of the drug reservoir 22, the injection needle 24 is disposed orthogonally to the drug-reservoir axis 22A and generally in the direction of the skin-contact surface 28. The injection needle 24 is in fluid communication with the interior of the drug reservoir 22 to allow a medicament in the drug reservoir 22 to be dispensed when the compressed, elastic power element 18 expands along the drug-reservoir axis 22A driving the plunger 30 distally into the drug reservoir 22.

Figure 3A:
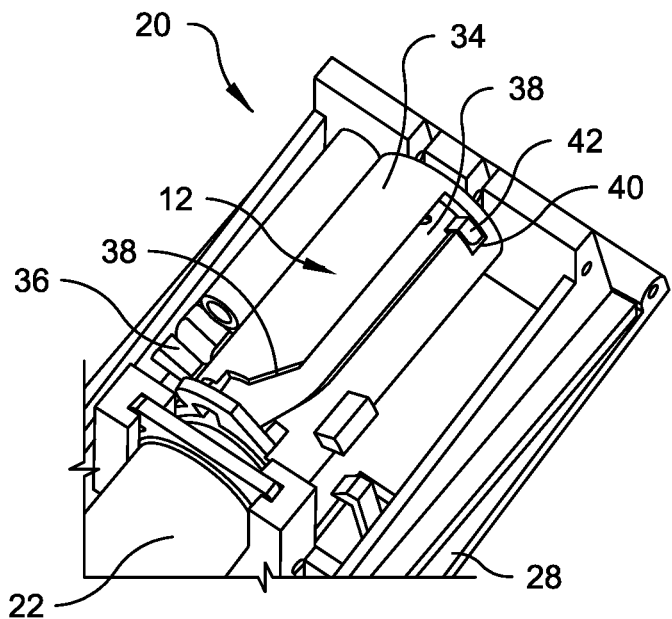
FIG. 3A is a top perspective view of the proximal portion of the patch injector of FIG. 1, showing a power pack in an inactive state.
Figure 3B:
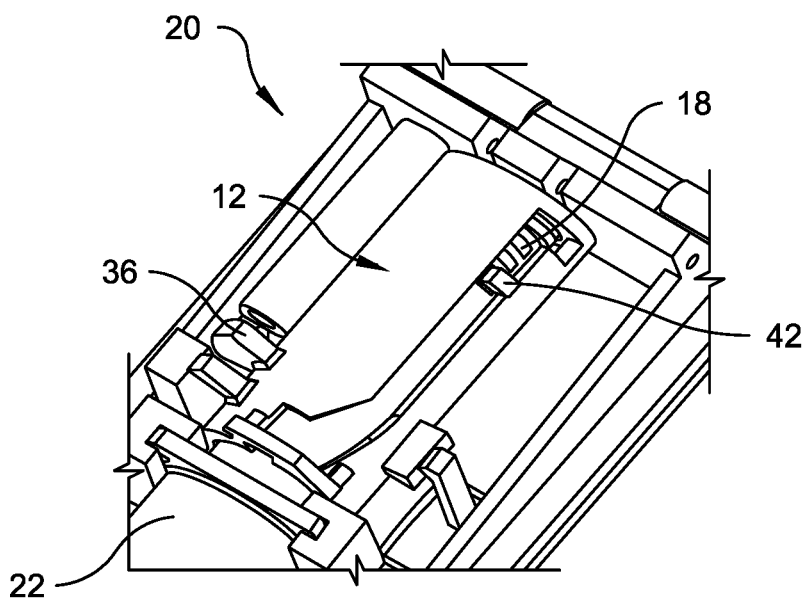
FIG. 3B is a top perspective view of the proximal portion of the patch injector of FIG. 1, showing the power pack in an activated state.

Referring now to FIG. 3A, a preferred embodiment of the locking element 20 is shown. In FIG. 3A, the power-pack module 12 includes an inner sleeve 32 and an outer sleeve 34. The outer sleeve 34 further includes a twisting element 36 and a groove 38 with a notch 40 at one end. The inner sleeve 32 includes an inner-piston lug 42 which extends outwardly through the groove 38 of the outer sleeve 34 and is configured to be able to slide within the groove 38. In the inactivated state of the patch injector 10, the inner-piston lug 42 of the inner sleeve 32 is releaseably retained in the notch 40 and the compressed, elastic power element 18 is maintained in compression. When the activation switch 44 (not shown in FIG. 3A; see FIG. 7) is depressed, the switch 44 presses against the twisting element 36 and causes relative rotational movement between the inner and outer sleeves 32, 34. This rotational movement allows the inner-piston lug 42 to move out of notch 40 and to slide within the groove 38 and the compressed, elastic power element 18 to expand axially (as seen in FIG. 3B).

Figure 4:
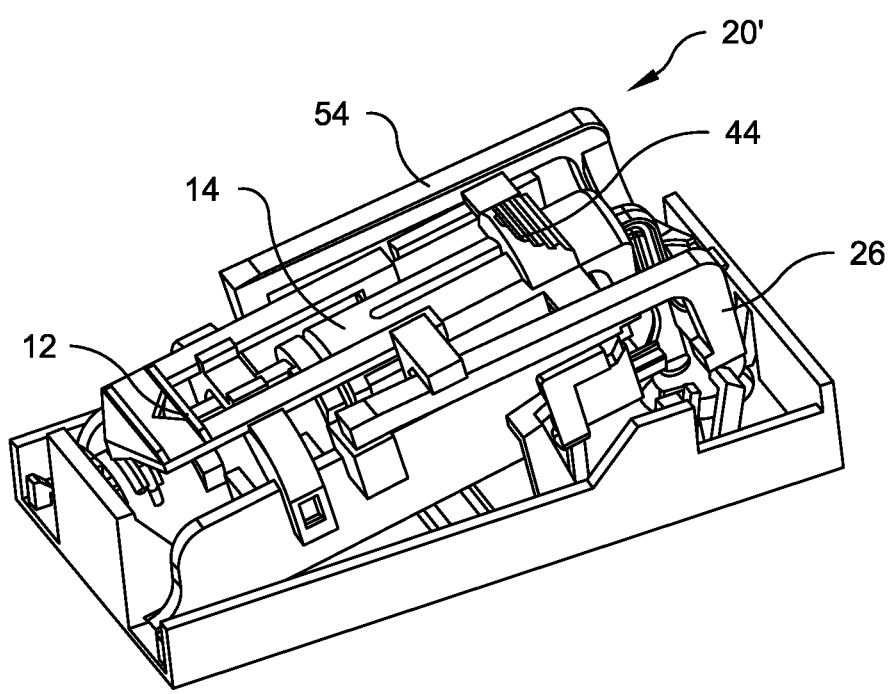
FIG. 4 is a top perspective view of the patch injector of FIG. 1 showing an alternative embodiment of the locking mechanism in accordance with the present invention.
Figure 5:
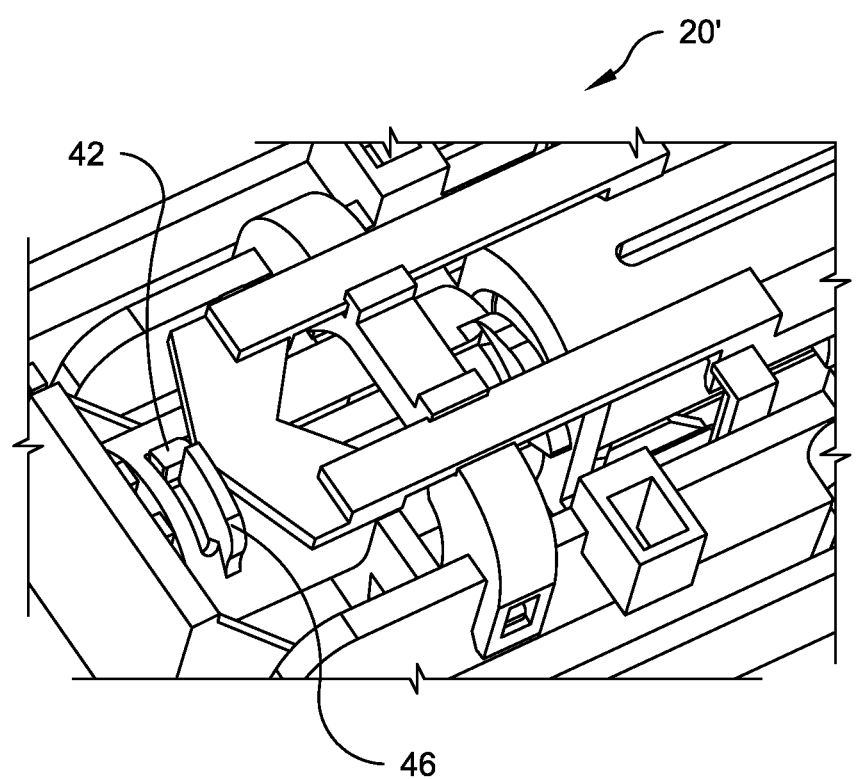
FIG. 5 is a top perspective view of the proximal portion of the locking mechanism of FIG. 4.

Referring to FIGS. 4-5, in another embodiment of the locking element, hereafter referred to as the locking element 20', the activation switch 44 is configured to slide in a direction parallel to the drug reservoir axis 22A. In this configuration, the inner-sleeve lug 42 is held in place in the notch 40 by a snap beam 46. When the activation switch 44 is displaced axially, the activation switch 44 contacts and displaces the snap beam 46 proximally such that inner-piston lug 42 is free to slide within the groove 38. In such an embodiment, the inner sleeve 32 is biased to twist relative to the outer sleeve 34 by the torsion of the compressed, elastic power element 18.

Figure 6:
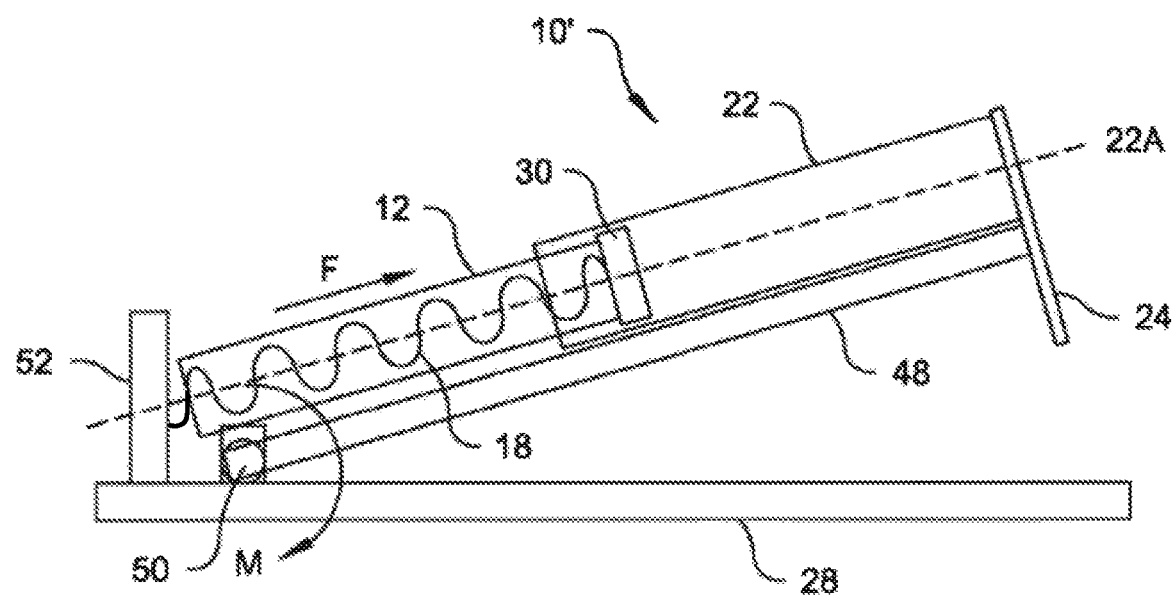
FIG. 6 is a schematic diagram of a second preferred embodiment of a patch injector in accordance with the present invention.

Referring now to FIG. 6, a second exemplary embodiment of the patch injector, hereafter referred to as the patch injector 10' is shown. In the patch injector 10', the power-pack module 12 and drug-cartridge module 14 are attached to an insertion-mechanism frame 48, which is, in turn, pivotably coupled at a pivot 50 to the skin-contact surface 28 of the drug recipient interface 16. The pivot 50 is offset from the drug-reservoir axis 22A. In this embodiment, the proximal end of the compressed, elastic power element 18 is fixedly secured to an extension 52 of the skin-contact surface 28. When the patch injector 10' is activated, as described above, the compressed, elastic power element 18 expands and exerts a force "F" along the drug-reservoir axis 22A. Since the pivot 50 is offset from the drug-reservoir axis 22A, the force "F" generates a bending moment "M" that rotates the insertion-mechanism frame 48 to drive the injection needle 24 into contact with and insertion in the drug recipient's skin. Thereafter, as the elastic power element 18 continues to expand, the force "F" exerted on the plunger 30 drives the plunger 30 into the drug reservoir 22 dispensing the medicament in the drug-reservoir while the bending moment "M" maintains the tip of the injection needle 24 below the skin surface of the drug recipient.

Figure 7:
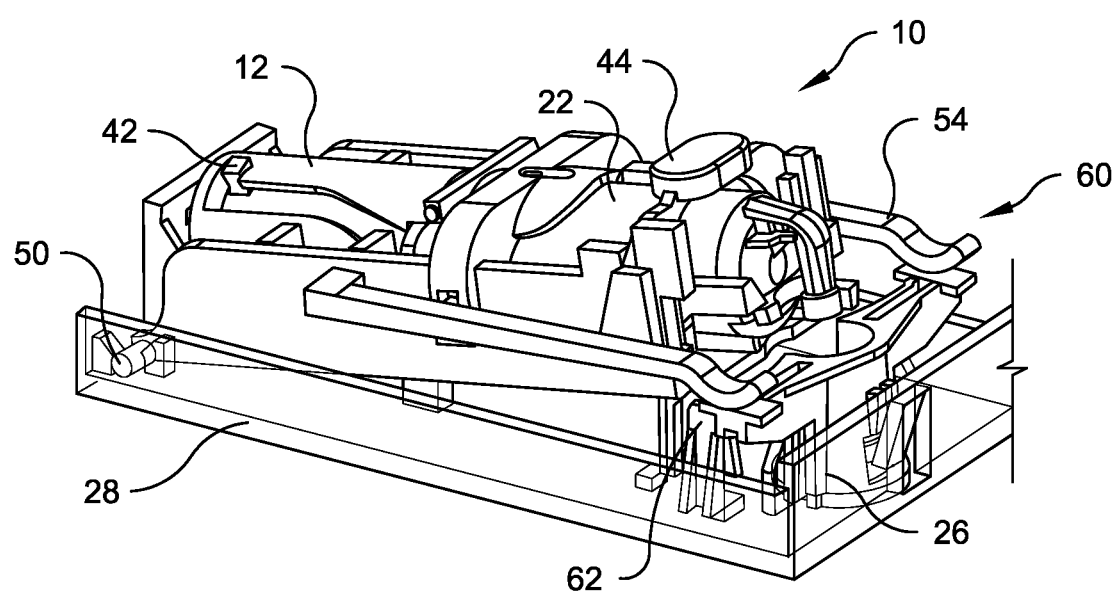
FIG. 7 is a top, right-side perspective view of the patch injector of FIG. 1, showing a needle protection mechanism in the pre-activation state in accordance with the present invention.
Figure 8:
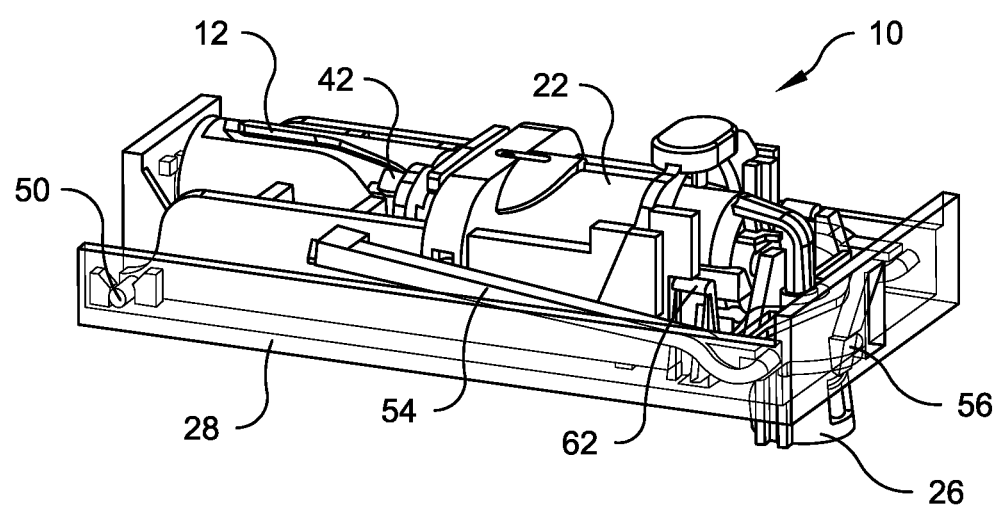
FIG. 8 is a top, right-side perspective view of the needle protection mechanism of FIG. 7, in the activated state in accordance with the present invention.

Referring now to FIGS. 7-8, the patch injector 10 is shown with an optional needle-protection mechanism 60. In the pre-activation state seen in FIG. 7, a detent or other needle-shield removable barrier 62 prevents the needle shield 26 from moving downward. In this position, the leaf springs 54 are not loaded and thus exert no force on the needle shield 7. When the patch injector 10 is activated, the compressed, elastic power element 18 causes the insertion-mechanism frame 48 to pivot as the pivot 50 is offset from the drug-reservoir axis 22A and the injection needle 24 to pass through the needle shield 26 and into the drug recipient's skin due to the moment "M" applied to the insertion-mechanism frame 48. The drug recipient's skin keeps the needle shield 26 in the up position. When the drug recipient has finished using the patch injector 10 and removes patch injector 10 from their skin, the needle shield 26 is no longer blocked and moves downward due to the force exerted by the elastic leaf springs 54. The needle shield 26 completely and permanently encapsulates the needle 24 to prevent unintended needle sticks (see FIG. 8). The needle shield 26 also includes a needle shield lock 56 which engages the insertion-mechanism frame 48 to prevent the needle shield 26 from being displaced upwards and exposing the injection needle 24. In addition, the needle shield 26 may be elastically coupled to the drug-cartridge module 14 and/or elastically deformable upon needle insertion such that it is configured to return to its unstressed state upon removal of the injector 10 from the skin.

A preferred method of using the patch injectors described above for the parenteral administration of a drug to a drug recipient having a skin surface has the following steps.

The skin-contact surface 28 of a the patch injector 10, 10' is adhesively attached to the skin surface of a drug recipient. A portion of the compressed, elastic power element 18 disposed in a power-pack module 12 of the patch injector 10, 10' is released to exit the power-pack module 12. The compressed, elastic power element 18 expands outwardly from the power-pack module 12 substantially parallel to the skin-contact surface. The infection-needle insertion mechanism 58 comprises an insertion-mechanism frame 48 and the injection-needle insertion mechanism 58 of the patch injector 10, 10' is driven with the expanding compressed, elastic power element 18 to extend the tip of the injection needle 24 outwardly from the skin-contact surface 28 to penetrate the skin surface of the drug recipient. The plunger 30 disposed in the drug reservoir 22 of the patch injector 10, 10' is displaced with the expanding compressed, elastic power element 18 to discharge the drug in the drug reservoir 22 through the tip of the injection needle 24. The needle protection mechanism 60 of the patch injector 10, 10' is driven with the expanding compressed, elastic power element 18 to protect the injection needle 24 with a needle shield 26 upon withdrawal of the injection needle 24 from the skin surface of the drug recipient.

The foregoing detailed description of the invention has been disclosed with reference to specific embodiments. However, the disclosure is not intended to be exhaustive or to limit the invention to the precise forms disclosed. Those skilled in the art will appreciate that changes could be made to the embodiments described above without departing from the broad inventive concept thereof. Therefore, the disclosure is intended to cover modifications within the spirit and scope of the present invention as defined by the appended claims.

All references, patent applications, and patents mentioned above are incorporated herein by reference in their entirety and are not to be construed as an admission that any of the cited documents constitutes prior art, or as an admission against interest in any manner.

We claim:

1. A patch injector for parenteral administration of a drug to a drug recipient having a skin surface, the patch injector comprising:
    a drug-cartridge module having a drug reservoir with a longitudinal drug-reservoir axis;
    a plunger movably disposed in the drug reservoir;
    a power-pack module attached to a proximal end of the drug-cartridge module;
    a compressed, elastic power element disposed in the power-pack module and coupled to the plunger, the compressed, elastic power element expandable along the longitudinal drug-reservoir axis;
    a drug-recipient interface module connected to the power-pack module, the drug-recipient interface module comprising:
    a skin-contact surface extending parallel to the longitudinal drug-reservoir axis;
    an injection-needle insertion mechanism driven by the compressed, elastic power element and wherein the power-pack module in which the compressed, elastic power element is disposed and the drug-cartridge module are attached to an insertion-mechanism frame pivotably coupled to the skin-contact surface by a pivot offset from the longitudinal drug-reservoir axis;
    an injection needle disposed at a distal end of the drug reservoir, the injection needle in fluid communication with the drug reservoir and oriented orthogonal to the drug reservoir and generally toward the skin-contact surface,
    characterized in that,
    the compressed, elastic power element is configured to displace the plunger distally into the drug reservoir and to move the injection needle toward the skin-contact surface when the compressed, elastic power element expands distally along the longitudinal drug-reservoir axis generating a bending moment in the injection-needle insertion mechanism, wherein a proximal end of the compressed, elastic power element disposed in the power-pack module is fixedly secured to an extension of the skin-contact surface and expansion of the compressed, elastic power element generates the bending moment that rotates the insertion-mechanism frame driving the injection needle toward the skin-contact surface.

2. The patch injector according to claim 1, further comprising a locking mechanism having an inactive state in which the compressed, elastic power element is maintained in compression and an active state in which the compressed, elastic power element expands along the longitudinal drug-reservoir axis driving the plunger distally into the drug reservoir.

3. The patch injector according to claim 2, wherein the power-pack module further comprises:
   an outer sleeve including a twisting element and a groove with a notch at one end of the twisting element;
   an inner sleeve disposed in the outer sleeve, the inner sleeve having an inner-piston lug which extends outwardly through the groove of the outer sleeve and is slideable in the groove,
   wherein the inner-piston lug is releasably retained in the notch when the locking mechanism is in the inactive state.

4. The patch injector according to claim 3, wherein the drug-recipient interface module further comprises an activation switch, wherein a depression of which causes relative rotational movement between the inner and outer sleeves, which releases the inner-piston lug from the notch and allows the compressed, elastic power element to expand along the longitudinal drug-reservoir axis.

5. The patch injector according to claim 1, wherein the drug-recipient interface module further comprises a needle-protection mechanism having a needle-shield configured to permanently encapsulate the injection needle when the patch injector is removed from the skin surface of the drug recipient.

\* \* \* \* \*